United States Patent
Kehoe et al.

(10) Patent No.: US 8,629,106 B2
(45) Date of Patent: Jan. 14, 2014

(54) AFFINITY PEPTIDES TOWARD BMP-2

(75) Inventors: John Kehoe, Wayne, PA (US); Daphne A. Salick, Lawrenceville, NJ (US); Carrie H. Fang, Pittstown, NJ (US); Chunlin Yang, Belle Mead, NJ (US); Abla Creasey, Morristown, NJ (US)

(73) Assignee: Janssen Biotech, Inc., Horsham, PA (US)

( * ) Notice: Subject to any disclaimer, the term of this patent is extended or adjusted under 35 U.S.C. 154(b) by 0 days.

(21) Appl. No.: 13/044,607

(22) Filed: Mar. 10, 2011

(65) Prior Publication Data

US 2011/0230406 A1 Sep. 22, 2011

Related U.S. Application Data

(60) Provisional application No. 61/314,239, filed on Mar. 16, 2010.

(51) Int. Cl.
| | |
|---|---|
| *A61K 38/18* | (2006.01) |
| *A61K 38/10* | (2006.01) |
| *A61K 38/04* | (2006.01) |
| *A61K 38/00* | (2006.01) |
| *C07K 7/08* | (2006.01) |
| *C07K 14/51* | (2006.01) |
| *C07K 17/02* | (2006.01) |

(52) U.S. Cl.
USPC .......... 514/8.8; 514/21.4; 514/21.5; 530/326; 530/327; 530/350

(58) Field of Classification Search
None
See application file for complete search history.

(56) References Cited

U.S. PATENT DOCUMENTS

| | | | |
|---|---|---|---|
| 5,504,190 A | 4/1996 | Houghten et al. | |
| 6,187,330 B1 | 2/2001 | Wang et al. | |
| 6,472,147 B1 | 10/2002 | Janda et al. | |
| 2003/0194445 A1 | 10/2003 | Kuhner et al. | |
| 2007/0066537 A1* | 3/2007 | Mickle et al. | 514/16 |
| 2007/0071675 A1 | 3/2007 | Wu et al. | |
| 2009/0326197 A1* | 12/2009 | Beyer et al. | 530/326 |

FOREIGN PATENT DOCUMENTS

| | | |
|---|---|---|
| WO | WO 2004/024199 A1 | 3/2004 |
| WO | WO 2010/042890 A2 | 4/2010 |

OTHER PUBLICATIONS

Kay et al., Screening Phage-Displayed Combinatorial Peptide Libraries, Methods 24, 2001, pp. 240-246.
M. Ishihara et al., Heparin-Carrying Polystyrene (HCPS)-Bound Collagen Substratum to Immobilize Heparin-Binding Growth Factors and to Enhance Cellular Growth, J Biomed Mater Res., 2001, pp. 536-544m vol. 56.
Liu, et al., Hyaluronate-heparin conjugate gels for the delivery of basic fibroblast growth factor (FGF-2), J Biomed Mater Res. 2001, pp. 128-135, vol. 62(1).
M. Geiger et al., Collagen Sponges for Bone Regeneration with rhBMP-2, Advanced Drug Delivery Reviews, 2003, pp. 1613-1629, vol. 55.
William F. McKay et al., A comprehensive clinical review of recombinant human bone morphogenetic protein-2 (INFUSE® Bone Graft), International Orthopaedics (SICOT), 2007, pp. 729-734, vol. 31.
Wong et al., Neurologic impairment from ectopic bone in the lumbar canal: a potential complication of off-label PLIF/TLIF use of bone morphogenetic protein-2 (BMP-2), The Spine Journal, 2008, pp. 1011-1018, vol. 8.
Zhao et al., The osteogenic effect of bone morphogenetic protein-2 on the collagen scaffold conjugated with antibodies, Journal of Controlled Release, 2009, pp. 1-8.
Leppert et al., Subcutaneous tissue cages for examination of slow release of materials from long-term implants, Biomaterials, 1990, pp. 46-49, vol. 11.
Dorsett-Martin et al., Rat Models of Skin Wound Healing, Sourcebook of Models for Biomedical Research, 2008, pp. 631-638.
PCT International Search Report for Application No. PCT/US2011/027904 dated Oct. 12, 2011.

* cited by examiner

*Primary Examiner* — Xiaozhen Xie
(74) *Attorney, Agent, or Firm* — Kirk Baumeister; Heather C. Brady

(57) ABSTRACT

We have disclosed affinity peptides toward BMP-2. More specifically we have disclosed an affinity biomatrix where the affinity peptide is covalently attached to a biocompatible, biodegradable polymer. The affinity biomatrix is useful in preparing controlled release devices for BMP-2.

7 Claims, 20 Drawing Sheets

FIG. 1.

SEQ ID NO: 1 AGLPLQSMSRLSYDSLS
SEQ ID NO: 2 AGPPGPYIAASAFLALK
SEQ ID NO: 3 AGYTSFALLKSAESTLP
SEQ ID NO: 4 AGFRWWHTQPAHTLSYT
SEQ ID NO: 5 AGYRRPIQPGPEAVSLL
SEQ ID NO: 6 AGRDSFNLLTSSPLPST
SEQ ID NO: 7 AGYRCSELPLYCST
SEQ ID NO: 8 AGSWCTHPAIGCLS
SEQ ID NO: 9 AGSPCSPGQLPLCPA
SEQ ID NO: 10 AGLQCSPPLPLYCEP
SEQ ID NO: 11 AGPRCPPMHFSVCLS
SEQ ID NO: 12 AGASCSPGLHPLCPG
SEQ ID NO: 13 AGSTCIPSMTPLCPS
SEQ ID NO: 14 AGRECLPQFGLPLCPD
SEQ ID NO: 15 AGSVCLAQYSATPLCPH
SEQ ID NO: 16 AGPDCRLSPLQPAVCVW
SEQ ID NO: 17 AGAHCLRDHMGLTSCIP
SEQ ID NO: 18 AGRLCHATVDGVAVGCLT
SEQ ID NO: 19 AGTVCPPDLTGLTAACYY
SEQ ID NO: 20 AGTLCGVDDYTGLTGCLA
SEQ ID NO: 21 AGIRCPVDAIGLTANCSY
SEQ ID NO: 22 AGRSCYREPSTMLYACTA

FIG. 8A.

SEQ ID NO: 23 Ac-AG-RDSFNLLTSSPLPST-SGGSGGSGG-OH

FIG. 12.

| | |
|---|---|
| SEQ ID NO: 24 | AGSSSFALLKSAESTLP |
| SEQ ID NO: 25 | AGSSSFALLKSAESTLP |
| SEQ ID NO: 26 | AGYTSFALSSSAESTLP |
| SEQ ID NO: 27 | AGYTSFALLKSAESSSS |
| SEQ ID NO: 28 | AGYTSFALLKSAESSSS |
| SEQ ID NO: 29 | AGSSSFNLLTSSPLPST |
| SEQ ID NO: 30 | AGRDSFNLSSSPLPST |
| SEQ ID NO: 31 | AGRDSFNLLTSSSSPST |
| SEQ ID NO: 32 | AGRDSFNLLTSSPLSSS |
| SEQ ID NO: 33 | AGYTSFALLKS |
| SEQ ID NO: 34 | AGRDSFNLLTS |

AFFINITY PEPTIDES TOWARD BMP-2

SEQUENCE LISTING

The instant application contains a Sequence Listing which has been submitted in ASCII format via EFS-Web and is hereby incorporated by reference in its entirety. Said ASCII copy, created on Apr. 11, 2011, is named RTX520US.txt and is 10,345 bytes in size.

FIELD OF THE INVENTION

The invention relates to specific affinity peptides toward bone morphogenic protein-2 (BMP-2). In addition, the invention relates to the use of these affinity peptides in controlled release devices for BMP-2.

BACKGROUND OF THE INVENTION

BMP-2 is a protein that belongs to the superfamily called transforming growth factor beta (TGF-beta). BMP-2 is known to induce the formation of bone and cartilage. For example, BMP-2 has been used to promote bone repair by surgically implanting a collagen matrix combined with the protein. BMP-2 is loaded into an absorbable collagen sponge as an aqueous suspension. The BMP-2 non-specifically associates with the collagen. However, due to the low binding capacity of the collagen fibrils toward BMP-2, and vice versa, BMP-2 can leak out of the collagen matrix. This leakage of BMP-2 from the collagen sponge causes undesirable exuberant and/or ectopic bone formation at or near the implant site. Undesirable bone growth leads to further complications, resulting in additional corrective surgery or surgeries for the patient.

Therefore, there is a need for a controlled release device for BMP-2 to eliminate the problematic side effect of bone formation in undesired locations. Standard methods for preparing controlled release devices include the use of polymeric matrices, typically in the form of microspheres, rods, sheets or pellets, which are used to encapsulate the active agent. A variety of techniques are known by which active agents can be incorporated into polymer matrices. Examples include solvent evaporation, spray drying, emulsification, melt blending and simple physical mixing of particles of discrete size or shape. None of these approaches may be applied to incorporate peptides or proteins into the polymers due to the delicate nature of these molecules. Peptides and proteins are susceptible to denaturation by solvents, by emulsification, by heat and, in particular, by terminal sterilization.

Therefore, there is a need for a method of making a controlled release device for BMP-2, where the method does not denature or otherwise inactivate the activity of the protein. A controlled release device for BMP-2 is also desired which provides a localized, sustained release of the protein, and thus avoids undesired ectopic bone formation.

SUMMARY OF THE INVENTION

We have described herein affinity peptides toward BMP-2. These affinity peptides, which have a specific affinity for BMP-2, are useful in preparing an affinity biomatrix. Controlled release devices for BMP-2 are also described which are prepared from the affinity biomatrix and BMP-2.

BRIEF DESCRIPTION OF THE FIGURES

FIG. 1. Amino acid sequences (affinity peptides) having a specific affinity toward BMP-2 containing linear and disulfide-constrained peptides.

FIG. 8A. Amino acid sequence (SEQ ID NO: 23) of the peptide used for the conjugation of SEQ ID NO: 6 to the collagen matrix containing an acetylated N-terminus and a linker.

FIG. 12. Amino acid sequences used to identify fragments of SEQ ID NO: 3 and SEQ ID NO: 6 that bind to BMP-2 and the amino acid sequences of the fragments that bind to BMP-2.

DETAILED DESCRIPTION OF THE INVENTION

We describe herein, affinity peptides toward BMP-2. In one embodiment, the BMP-2 is human recombinant BMP-2. An affinity peptide toward BMP-2 indicates that the peptide has a specific binding affinity toward BMP-2. The peptide may be either linear or disulfide constrained. In one embodiment, the affinity peptide toward BMP-2 is any one of the affinity peptides shown in FIG. 1. In another embodiment, the affinity peptides may be a fragment of any one of the affinity peptides shown in FIG. 1. While the affinity peptide has specific affinity toward BMP-2, the affinity peptide does not interfere with the bioactivity of BMP-2. These affinity peptides are useful in the preparation of controlled release devices for BMP-2.

The affinity peptides toward BMP-2 shown in FIG. 1 were identified using a pIX phage display technology described in U.S. Pat. No. 6,472,147. Primary peptide phage libraries with high complexity ($10^9$ peptides sequences per library) were used to select for affinity peptides toward BMP-2. More specifically, biotinylated-BMP-2 was immobilized on a streptavidin-coated ELISA plate and phage which display the peptide sequences on the pIX minor coat protein were introduced. The phage that did not bind to BMP-2 were washed away and the phage that did bind to BMP-2 were isolated and amplified. The isolated phage that bound to BMP-2 were used as input for the second round of the selection following the procedure stated above for a total of three rounds. At the end of the third round the phage that bound to BMP-2 were sequenced to determine the peptide which is responsible for binding to BMP-2. Peptides having affinity toward BMP-2 are listed in FIG. 1.

Figure 2:
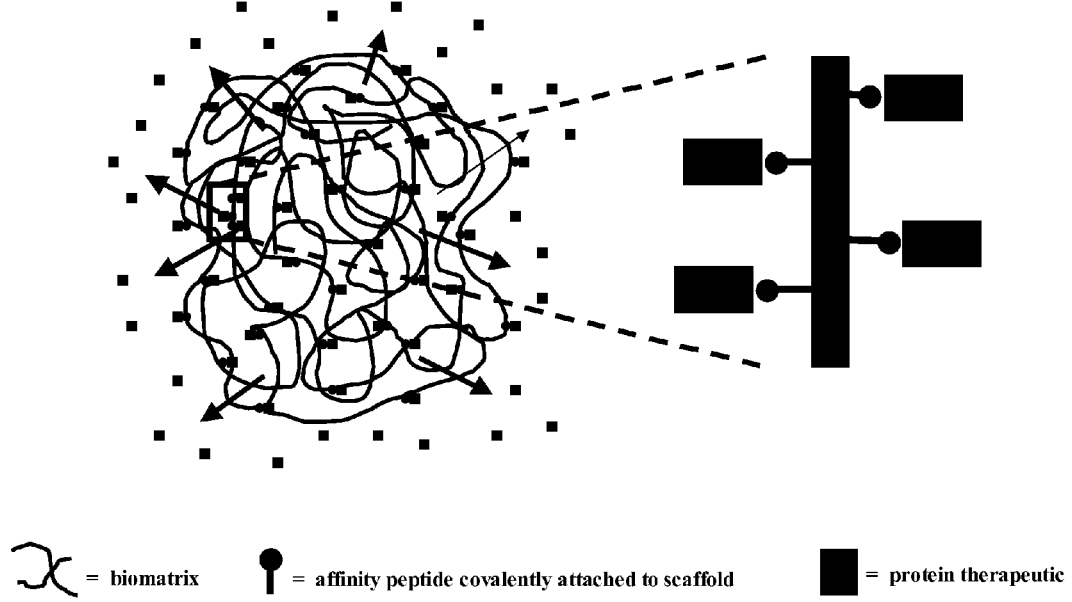
FIG. 2. Pictorial representation of the controlled release device comprising an affinity biomatrix and BMP-2.

The affinity peptides toward BMP-2 are useful in preparing an affinity biomatrix. The affinity biomatrix is prepared by covalently attaching at least one affinity peptide toward BMP-2, as described above, to a biocompatible, biodegradable polymer. Furthermore, the affinity biomatrix is useful as a controlled release device for BMP-2. A representative embodiment is shown pictorially in FIG. 2. The controlled release device for BMP-2 comprises an affinity biomatrix and BMP-2.

The biocompatible, biodegradable polymer used to prepare the affinity biomatrix may be natural polymers, synthetic polymers, and combinations thereof. The biodegradable polymers readily break down into small segments when exposed to moist body tissue. The segments then either are absorbed by the body, or passed by the body. More particularly, the biodegraded segments do not elicit permanent chronic foreign body reaction, because they are absorbed by the body or passed from the body, such that no permanent trace or residual of the segment is retained by the body.

Suitable natural polymers include, but are not limited to proteins such as, collagen, elastin, keratin, silk, glucosaminoglycans (GAGs), thrombin, fibronectin, gelatin, fibrin, tropoelastin, polypeptides, laminin, proteoglycans, fibrin glue, fibrin clot, platelet rich plasma (PRP) clot, platelet poor plasma (PPP) clot, self-assembling peptide hydrogels, and atelocollagen; polysaccharides such as, starch, pectin, cellulose, alkyl cellulose (e.g. methylcellulose), alkylhydroxyalkyl cellulose (e.g. ethylhydroxyethyl cellulose), hydroxyalkyl cellulose (e.g. hydroxyethyl cellulose), cellulose sulfate, salts of carboxymethyl cellulose, carboxymethyl cellulose, carboxyethyl cellulose, chitin, carboxymethyl chitin, hyaluronic acid, salts of hyaluronic acid, alginate, crosslinked alginate alginic acid, propylene glycol alginate, glycogen, dextran, dextran sulfate, curdlan, pectin, pullulan, xanthan, chondroitin, chondroitin sulfates, carboxymethyl dextran, carboxymethyl chitosan, chitosan, heparin, heparin sulfate, heparan, heparan sulfate, dermatan sulfate, keratan sulfate, carrageenans, chitosan, starch, amylose, amylopectin, poly-N-glucosamine, polymannuronic acid, polyglucuronic acid polyglucuronic acid), and derivatives; polynucleotides such as, ribonucleic acids, deoxyribonucleic acids, and combinations thereof.

In one embodiment the natural polymer is collagen. In another embodiment the natural polymer may be obtained from decellularized tissue. The decellularized tissue may be obtained from autogeneic tissue, allogeneic tissue or xenogeneic tissue. Suitable decellularized tissues include, but are not limited to skin, periosteum, perichondrium, synovium, fascia, mesenter, bone, sinew, and the like.

Examples of suitable synthetic polymers include, but are not limited to aliphatic polyesters, poly(amino acids), copoly (ether-esters), polyalkylene oxalates, polyamides, poly(iminocarbonates), polyorthoesters, polyoxaesters, polyamidoesters, polyoxaesters containing amine groups, poly (anhydrides), polyphosphazenes, biomolecules and blends thereof. For the purpose of this invention aliphatic polyesters include, but are not limited to homopolymers and copolymers of lactide (which includes lactic acid, d-, l- and meso lactide), glycolide (including glycolic acid), epsilon-caprolactone, p-dioxanone (1,4-dioxan-2-one), trimethylene carbonate (1,3-dioxan-2-one), alkyl derivatives of trimethylene carbonate, delta-valerolactone, beta-butyrolactone, gamma-butyrolactone, epsilon-decalactone, hydroxybutyrate (repeating units), hydroxyvalerate (repeating units), 1,4-dioxepan-2-one (including its dimer 1,5,8,12-tetraoxacyclotetradecane-7,14-dione), 1,5-dioxepan-2-one, 6,6-dimethyl-1,4-dioxan-2-one 2,5-diketomorpholine, pivalolactone, alpha, alpha-diethylpropiolactone, ethylene carbonate, ethylene oxalate, 3-methyl-1,4-dioxane-2,5-dione, 3,3-diethyl-1,4-dioxan-2, 5-dione, 6,8-dioxabicycloctane-7-one and polymer blends thereof.

Suitable aliphatic polyesters include, but are not limited to homopolymers and copolymers of lactide (which includes lactic acid, D-,L- and meso lactide), glycolide (including glycolic acid), epsilon-caprolactone, p-dioxanone (1,4-dioxan-2-one), trimethylene carbonate (1,3-dioxan-2-one), alkyl derivatives of trimethylene carbonate, delta-valerolactone, beta-butyrolactone, gamma-butyrolactone, epsilon-decalactone, hydroxybutyrate (repeating units), hydroxyvalerate (repeating units), 1,4-dioxepan-2-one (including its dimer 1,5,8,12-tetraoxacyclotetradecane-7,14-dione), 1,5-dioxepan-2-one, 6,6-dimethyl-1,4-dioxan-2-one and polymer blends thereof.

In one embodiment, the biocompatible, biodegradable polymer and the affinity peptides toward BMP-2 have suitable reactive groups and corresponding functional groups to covalently attach the affinity peptide to the polymer. The reactive groups and functional groups may be on the polymer, the affinity peptide, and combinations thereof. Suitable reactive groups include, but are not limited to aryl azide, carbodiimide, hydrazine, hydroxymethyl phosphine, imidoester, isocyanate, carbonyl, maleimide, NHS-ester, PFP-ester, thiol, pyridyl disulfide and/or vinyl sulfone and the like. Suitable functional groups include, but are not limited to hydroxyl, carboxyl, aldehyde, ester, thiol, amine, alkene, alkyne, alkyl halide, hydrazine and/or azide functional groups. One of skill in the art of organic chemistry or polymer chemistry would be able to functionalize the affinity peptide and the polymer with the above suitable reactive groups and corresponding functional groups to covalently attach the affinity peptide to the polymer. For example, amine functional groups on the lysine residues displayed from collagen can be coupled to the C-terminal carboxyl group of an affinity peptide using simple carbodiimide chemistry.

Optionally, a linker sequence may be added to the peptides shown in FIG. 1 in order to increase the availability of the affinity peptide to bind to BMP-2. The linker sequence can be $(SGG)_n$ or $(XXX)_n$, where X may be any combination of serine, glycine, alanine or threonine. In one embodiment, the number of repeat units n is from about 1 to about 10. In another embodiment, the number of repeat units n is from about 3 to about 5.

For example, the affinity biomatrix may be prepared from soluble and/or fibrillar Type I bovine collagen. Briefly, a homogenized collagen suspension in water, having a concentration of from about 10 mg/mL to about 100 mg/mL, is cast into a mold and then lyophilized. After a thermal dehydration step, the affinity peptides are conjugated to the collagen using 1-ethyl-3[3-dimethylaminopropyl]carbodiimide hydrochloride (EDC)/N-hydroxysulfosuccinimide (Sulfo-NHS) coupling chemistry The collagen affinity biomatrix prepared in this manner is in the form of a porous three-dimensional foam scaffold.

The affinity biomatrix is useful as a controlled release device for BMP-2. The controlled release device for BMP-2 comprises an affinity biomatrix and BMP-2. The amount of BMP-2 that may be loaded into the affinity biomatrix is dependent upon the amount of affinity peptide conjugated to the biocompatible, biodegradable polymer. The amount of affinity peptide present on the biocompatible, biodegradable polymer may be equal to or greater than the desired amount of BMP-2 in the controlled release device. Therefore there may be at least 1 mole of affinity peptide to 1 mole of BMP-2 to be delivered. One of skill in the art will be able to determine how much BMP-2 is desired in the controlled release device for the bone repair. The controlled release device may be in the form of sponges, particles, injectable gels or liquids, membranes, films, fibers and fiber based scaffolds, and the like.

In one embodiment, the controlled release device is in the form of an injectable gel or liquid, where the affinity biomatrix is in an aqueous solution and contains BMP-2. Examples of suitable aqueous solutions include, but are not limited to physiological buffer solution, saline, water, buffered saline, phosphate buffer solution, Hank's balanced salts solution, PBS, Tris buffered saline, Hepes buffered saline, and mixtures thereof. Polymers useful for preparing an injectable gel or liquid device may be selected from the natural or synthetic polymers described above. In the case of an injectable liquid or gel, the affinity biomatrix may be present in the aqueous solution in the amount of from about 10 mg/mL to about 150 mg/mL.

Optionally, synthetic bone minerals can also be incorporated into the controlled release device for BMP-2 to tailor the mechanical properties for a particular application. For example, bioactive inorganics can be incorporated, which include but are not limited to hydroxyapatite, fluoro-hydroxyapatite, and/or silicate, to increase the tensile strength of the biomatrix.

The BMP-2 controlled release device may optionally also have cells incorporated therein. Suitable cell types include, but are not limited to, osteocytes, osteoblasts, chondrocytes, stem cells, pluripotent cells, umbilical cord cells, stromal cells, mesenchymal stem cells, bone marrow cells, embryonic stem cells; precursor cells derived from adipose tissue; peripheral blood progenitor cells; stem cells isolated from adult tissue; genetically transformed cells; and combinations thereof.

The controlled release device for BMP-2 can be sold as a kit containing a sterile affinity biomatrix and sterile lyophilized powder of BMP-2. The affinity biomatrix and BMP-2 contained in the kit can be sterilized using conventional sterilization procedures which may include, but are not limited to e-beam, gamma irradiation and aseptic sterile preparation methods.

The controlled release device for BMP-2 allows one to locally deliver BMP-2 in a controlled manner. The controlled release device may be implanted or injected in the site where bone repair or regeneration is desired. This localized delivery helps to eliminate the undesired effects of exuberant and/or ectopic bone formation caused by the current methods of delivery. This reduction in ectopic bone formation in turn would decrease the failure rates of these implants and thus increase the quality of life for the patient.

EXAMPLES

Example 1

BMP-2 Affinity Peptide Selection using Phage Display

Primary peptide phage libraries with high complexity ($10^9$ peptides sequences per library) were used to select for affinity peptides toward BMP-2. More specifically, biotinylated-BMP-2 was immobilized on a streptavidin-coated ELISA plate and phage which display the peptide sequences on the pIX minor coat protein were introduced. The phage that did not bind to BMP-2 were washed away and the phage that did bind to BMP-2 were isolated and amplified. The isolated phage that bound to BMP-2 were used as input for the second round of the selection following the procedure stated above for a total of three rounds.

Enzyme linked immunosorbent assay (ELISA) plates were loaded with 200 microliters per well of streptavidin at 5 micrograms/mL in phosphate buffered saline (PBS) and held at 4° C. overnight. Two wells were coated per selection. The streptavidin-coated ELISA plates were then washed three times with tris buffered saline containing Tween 20 (TBST) using a 96 well ELISA plate washer and then loaded with biotinylated BMP-2 (R&D Systems Minneapolis, Minn., Item #355-BM/CF) at a concentration of five micrograms/mL in PBS. The plates were held at room temperature for 30 minutes. Meanwhile, eppendorf tubes (1 mL volume) were blocked (one per library) using 1 mL of 3% dehydrated milk in TBST. The eppendorf tubes were tumbled at room temperature for 30 minutes. Two MC1061F' GII *E. coli* cultures were started in 2×YT media supplemented with tetracycline on a shaker at 37° C. The blocking solution in the eppendorf tubes was then discarded and replaced with 100 microliters of peptide library and 300 microliters of 3% milk in TBST. This solution was tumbled at room temperature for 1 hour. While blocking the primary peptide phage libraries, the streptavidin-coated, BMP-2-loaded wells were washed 3 times with TBST using a plate washer. The plates were then blocked with 250 microliters of 3% milk in TBST for 1 hour at room temperature. The blocking solution was removed from each well and discarded and the peptide phage library solution was introduced to each respective well at a volume of 200 microliters per well. This was held at room temperature for 1 hour. The library-milk solutions were then removed from each well and discarded and the wells were washed 3 times by hand with TBST. 200 microliters of mid-log phage MC1061F' GII *E. coli* were introduced to each well and incubated at 37° C. for 30 minutes. The infected bacteria were grown for 4 hours at 37° C. in 50 mL of 2×YT media supplemented with tetracycline. Next, the bacteria were separated by centrifugation and phage were precipitated using a PEG/NaCl solution. The PEG-precipitated phage were used in round two and the above process was repeated for a total of three cycles of the selection process.

At the end of the third round the phage that bound to BMP-2 were sequenced to determine the peptide which is responsible for binding to BMP-2. The phage-infected bacteria were plated out for single plaques in top agar with MC1061F'GII *E. coli*. The resultant plaques were used to isolate phage that bind to BMP-2 using ELISA. Once single phage were identified, the phage that bound to BMP-2 were amplified, PEG-precipitated and sequence analysis was performed. Peptides having affinity toward BMP-2 are listed in FIG. 1.

These phage were used for the phage titration described in Example 2 and the confirmatory and cross-reactivity phage ELISA assay described in Example 3.

Example 2

BMP-2 Selection Output Phage Titration

A phage titration was performed to determine the concentration of phage which resulted from the PEG precipitation of the phage that bound to BMP-2 described in Example 1.

E. coli MC1061F'GII were grown in 2xYT media supplemented with tetracycline for 2-3 hours at 37° C. on a shaker (180-250 rpm). In a 96-well plate, phage dilutions were performed, assuming the PEG precipitated stock solutions contain $10^{12}$ phage/mL. Briefly, 100 microliters of 2xYT media was introduced to the wells of a 96-well plate. To column 1, 10 microliters of respective phage stock solutions were introduced. Serial 1:10 dilutions were performed across the plate to column 12 resulting in phage concentrations of $10^{10}$, $10^9$, $10^8$, $10^7$, $10^6$, $10^5$, $10^4$, $10^3$, $10^2$, $10^1$, $10^0$, $10^{-4}$, respectively, where each row contains a distinct phage. For phage plaque growth, 1.5 microliters of each respective phage dilution series was introduced to an LB/Tetracycline/X-Gal agar plate coated with a solidified top agar/bacteria suspension. Plates were incubated upside down at 37° C. overnight. After overnight incubation, a dilution was chosen where the phage plaques are well separated and could be counted. The following formula was used to calculate the titer: (# plaques)(66.7)($10^{dilution\ number-1}$)×100=phage/mL, where 66.7 is the dilution factor of the phage in each well and the dilution number is the number of dilutions performed until phage plaques could be counted. Multiplication by 100 yields the number of phage/mL in the stock phage suspension.

Calculated phage concentrations are shown in Table 1. Phage concentrations obtained were used to perform the dilutions for the confirmatory and cross-reactivity phage ELISA assay described in Example 3.

TABLE 1

| SEQ ID NO. | Phage/mL |
| --- | --- |
| 1 | 1.4007E+12 |
| 2 | 1.334E+12 |
| 3 | 1.0672E+12 |
| 4 | 1.1339E+12 |
| 5 | 4.669E+11 |
| 6 | 6.67E+11 |
| 7 | 9.338E+11 |
| 8 | 5.336E+11 |
| 9 | 1.4007E+12 |
| 10 | 1.334E+12 |
| 11 | 4.669E+11 |
| 12 | 1.0005E+12 |
| 13 | 5.336E+11 |
| 14 | 1.334E+12 |
| 15 | 8.671E+11 |
| 16 | 8.004E+11 |
| 17 | 1.334E+12 |
| 18 | 1.6675E+12 |
| 19 | 8.004E+11 |
| 20 | 7.337E+11 |
| 21 | 2.1344E+12 |
| 22 | 1.1339E+12 |

Example 3

Confirmatory and Cross-Reactivity Phage ELISA Assay

In this experiment, we are confirming the binding of the phage identified in Example 1 to BMP-2. In addition, we are also testing that the phage do not exhibit binding to human serum albumin and hIgG.

96-well black ELISA plates were coated with streptavidin (Rows A through D), hIgG (Rows E and F) and human serum albumin (Rows G and H), at a concentration of 5 micrograms/mL in PBS. Plates were incubated overnight at 4° C. Plates were washed 3 times with TBST using a plate washer. To the streptavidin-coated wells in rows C and D, 100 microliters of a 4 micrograms/mL solution of biotinylated-BMP-2 (R&D Systems, Minneapolis, Minn., Item number 355-BM/CF), was introduced and allowed to sit at room temperature for 30 minutes. To all other wells, 100 microliters of PBS was introduced. The plates were again washed 3 times with TBST using the plate washer. The wells were then blocked with 250 microliters of a 3% dehydrated milk suspension in TBST and allowed to sit at room temperature for a minimum of 1 hour. Using phage concentrations determined by the phage titrations, dilutions of the phage stock solutions were performed in a separate 96-well plate to result in phage concentrations of $10^{10}$, $10^9$, $10^8$, $10^7$, $10^6$ and $10^5$ phage/well. After blocking, the ELISA plate was washed 3 times with TBST and 100 microliters of the phage dilutions were introduced to the respective ELISA plates and allowed to sit at room temperature for a minimum of 1 hour. The ELISA plate was again washed 3 times with TBST using the plate washer and 100 microliters of an HRP-conjugated Anti-M13 Phage Mab (1:5000 dilution in PBS) was introduced to each well. The plates were allowed to sit at room temperature for 1 hour after which time the plates were washed 3 times with TBST. Next, a POD HRP-substrate was introduced to each well. The luminescence was read using a luminometer set with a gain of 150.

Figure 3:
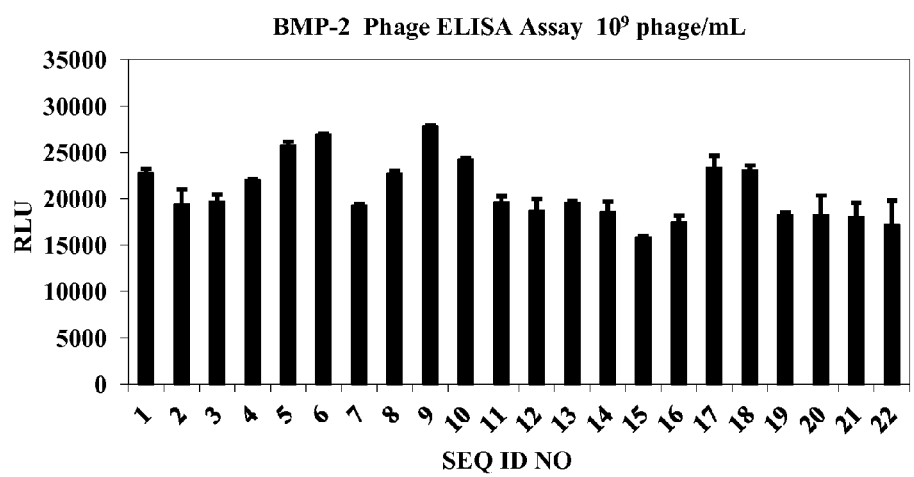
FIG. 3. BMP-2 phage ELISA assay confirming the phage-displayed peptides generated from the phage selection are binding to BMP-2.
Figure 4A:
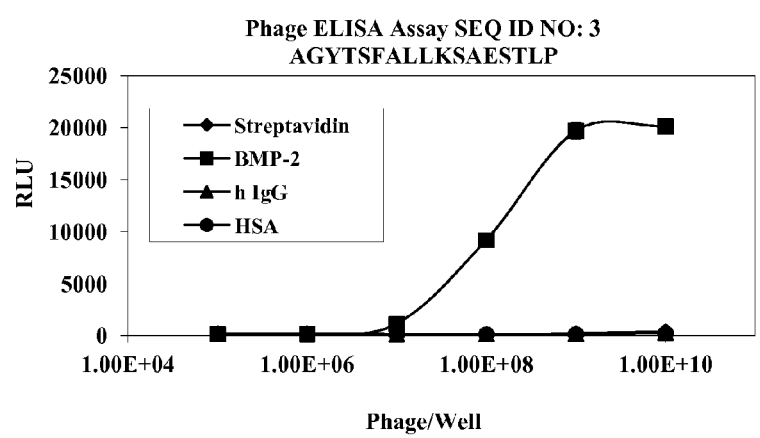
FIG. 4A. Confirmatory and cross-reactivity phage ELISA assay with increasing number of phage/well showing phage binders that are minimally cross reactive.
Figure 4B:
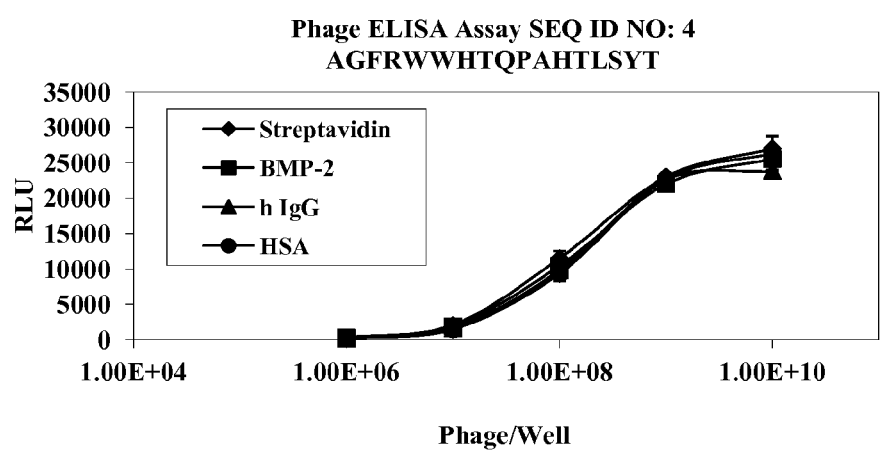
FIG. 4B. Confirmatory and cross-reactivity phage ELISA assay with increasing number of phage/well showing phage binders that are highly cross reactive.
Figure 4C:
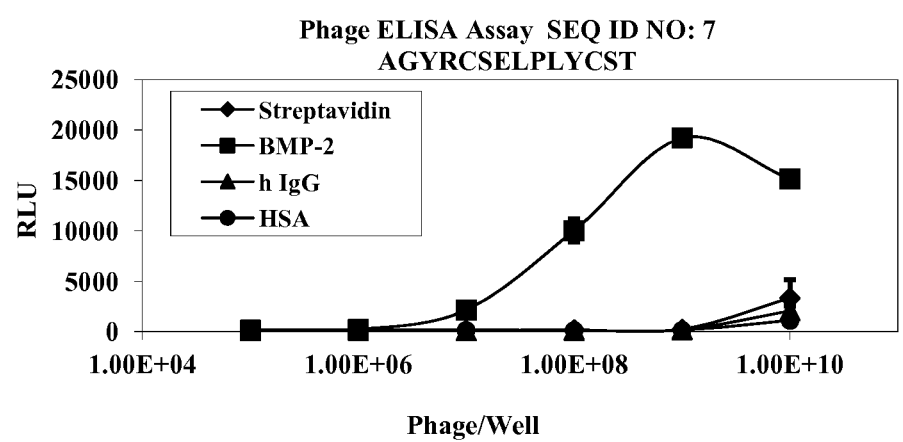
FIG. 4C. Confirmatory and cross-reactivity phage ELISA assay with increasing number of phage/well showing phage binders that are cross reactive at high phage concentrations ($10^{10}$ phage/well).
Figure 5A:
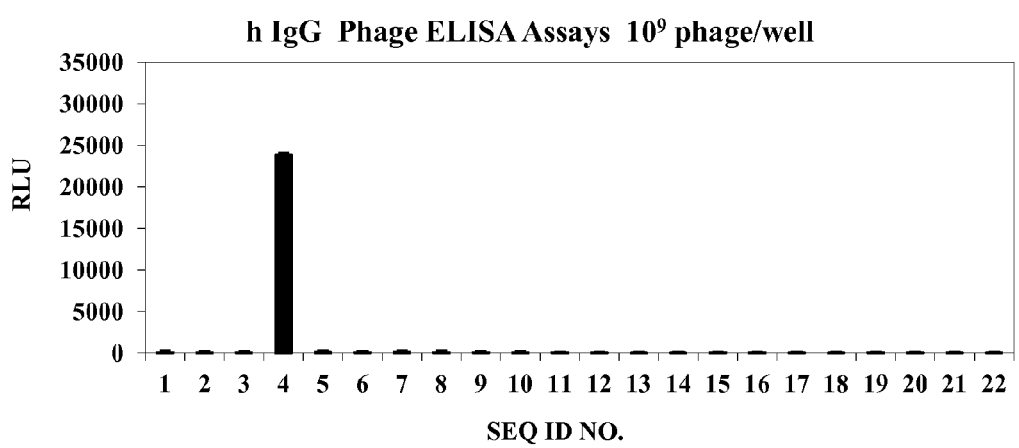
FIG. 5A. Cross reactivity phage ELISA assays toward human IgG.
Figure 5B:
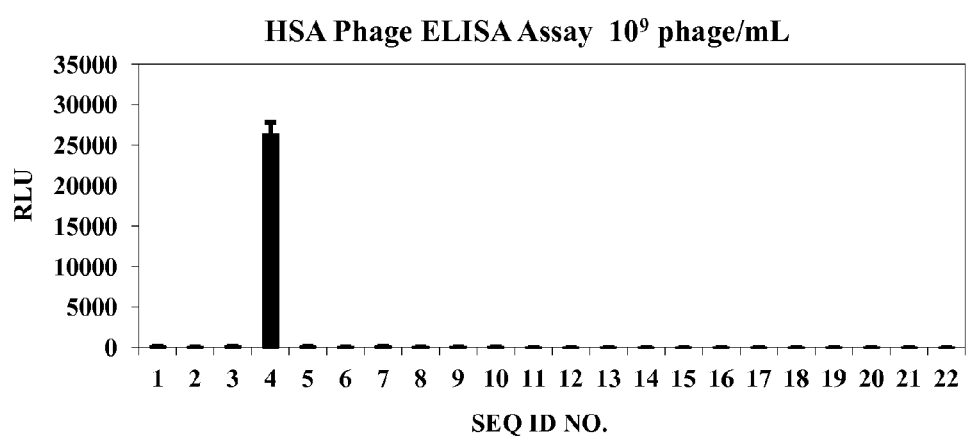
FIG. 5B. Cross reactivity phage ELISA assays toward human serum albumin (HSA).

The phage ELISA data in FIG. 3, FIG. 4 and FIG. 5 show relative luminescence and have an N value of 2. Data in FIG. 3 confirms the binding of the isolated phage to BMP-2. Data in FIG. 4 and FIG. 5 show that the phage are minimally cross-reactive with hIgG and HSA respectively, with the exception of SEQ ID NO: 4, which binds to both hIgG and HSA.

Example 4

Amplified Luminescent Proximity Homogenous Assay (ALPHA)

Concentration dependent binding efficiency of BMP-2 to the affinity peptides was evaluated using an ALPHA assay.

Diluted stock of biotinylated BMP-2 (R&D Systems, Minneapolis, Minn., Item number 355-BM/CF) at 3.3 micrograms/ml was prepared in 2× assay buffer (PBS, 0.01% Tween-80, 0.05% BSA). Chemically synthesized peptides having SEQ ID NO: 1, SEQ ID NO: 2, SEQ ID NO: 3, and SEQ ID NO: 6 were prepared using standard, automated Fluorenylmethyloxycarbonyl (Fmoc) solid phase peptide synthesis procedures. Each peptide solution for the assay was prepared from a 100 microgram/mL stock solution. The stock solution was serially diluted in ½ log steps in assay buffer resulting in peptide concentrations of 100, 33.3, 11.1, 3.70, 1.23, 0.41, 0.14, 0.046, 0.015, 0.0051, 0.0017 and 0.00056 micrograms/mL. Subsequently, serially diluted peptides were added to the corresponding wells containing the 10 microliters of the 3.3 microgram/mL solution of biotinylated BMP-2. Final assay test concentration for biotinylated BMP-2 was 0.825 micrograms/mL. Final peptide concentrations were 25, 8.3, 2.8, 0.93, 0.31, 0.10, 0.03, 0.01, 0.003, 0.001, 0.0003 and 0.0001 micrograms/mL. Next, Nickel (Ni)-acceptor and streptavidin (SA)-donor beads (Perkin Elmer, Waltham, Mass., Item number 6760619M) were diluted 1:100 in assay buffer prior to adding 20 microliters to each test well. Controls included BMP-2 alone in three different concentrations as well as SA beads with no peptide. The plate was made light-safe with an aluminum seal and shaken for 45 minutes on a table-top shaker at room temperature. The emission of the plate was read using a dual wavelength fluorometer (Perkin Elmer (Waltham, Mass.) Envision 2101 Multilabel Reader).

Figure 6:
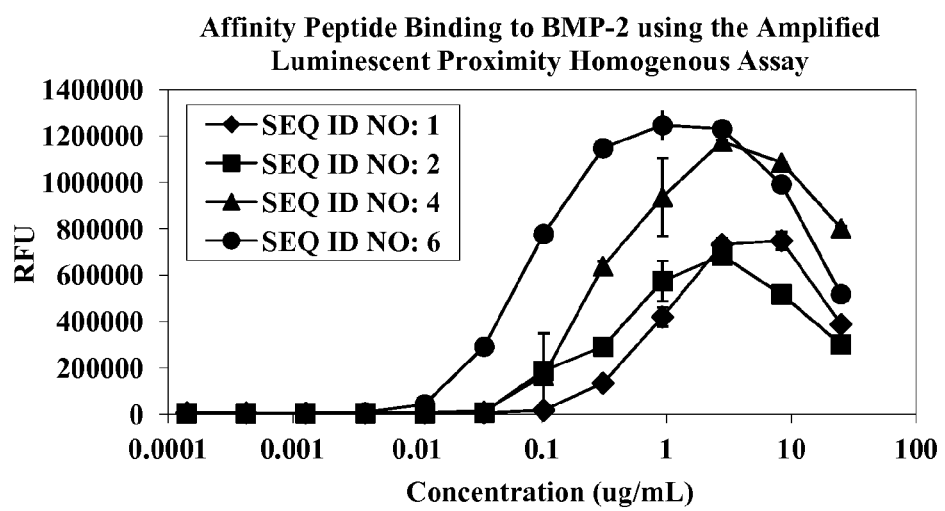
FIG. 6. Concentration dependent binding of the affinity peptides toward BMP-2 using an amplified luminescent proximity homogenous assay (ALPHA).

The ALPHA data in FIG. 6 was normalized to molar concentration based on the molecular weights of the peptide sequences. The data in FIG. 6 shows the concentration-dependent binding of the peptides to BMP-2. Peptide sequences were ranked according to their concentration-dependent binding to BMP-2 as follows; SEQ ID NO: 6>SEQ ID NO: 3>SEQ ID NO: 2>SEQ ID NO: 1.

Example 5

Surface Plasmon Resonance (SPR)

Peptide binding affinity to BMP-2 was evaluated for SEQ ID NO: 3 and SEQ ID NO: 6 by surface plasmon resonance measurements. Measurements were performed on a Biacore S51 (Biacore Life Sciences, Piscataway, N.J.) instrument using a CM4 Series-S sensor chip. rhBMP-2 (R&D Systems, Minneapolis, Minn., Item number 355-BM/CF) was immobilized on the sensor chip using 1-ethyl-3[3-dimethylaminopropyl]carbodiimide hydrochloride (EDC)/N-hydroxysuccinimide (NHS) coupling chemistry. BMP-2 affinity peptides were flowed over the BMP-2 functionalized chip at a concentration of 5 micromolar and changes in the refractive index were recorded. Data were fit to a 1:1 Langmuir binding model using Biacore Analysis Software (Biacore Life Sciences, Piscataway, N.J.).

The data shown in Table 2 are average equilibrium dissociation constants with an N value of 3. Data show average equilibrium dissociation constants between 300 and 400 nM.

TABLE 2

|  | $K_D$ (M) |
| --- | --- |
| SEQ ID NO: 6 | $3.03 \times 10^{-7}$ M ($\pm 1.77 \times 10^{-8}$) |
| SEQ ID NO: 3 | $3.98 \times 10^{-7}$ M ($\pm 5.94 \times 10^{-8}$) |

Example 6

Alkaline Phosphatase Bioactivity Assay

In this experiment, we determined if the affinity peptides would interfere with the cell surface receptor binding to BMP-2 using mouse osteoblasts. The alkaline phosphatase (ALP) production was monitored the presence of BMP-2 with and without affinity peptides.

Passage two MCHT-1/26 cells (mouse osteoblast cell line) were plated out in a 96 well plate the night before at 4500 cells/well. Cells were stimulated with serial dilution of BMP-2 in a range 0-1000 ng/ml in the presence or absence of 3 dilutions of peptide SEQ ID NO: 6 at 16, 160 and 800 nM. After incubation at 37° C. for 3 days, cells were lysed with lysis buffer (250 mM NaCl, 25 mM $MgCl_2$ and 100 mM Tris, pH=8.0) overnight at 37° C. One third of the lysate was used for alkaline phosphatase assay with p-nitrophenylphosphate. The reaction was carried out at 37° C. for one to two hours. Next, the plate was read on an absorbance plate reader at a wavelength of 405 nm.

Figure 7:
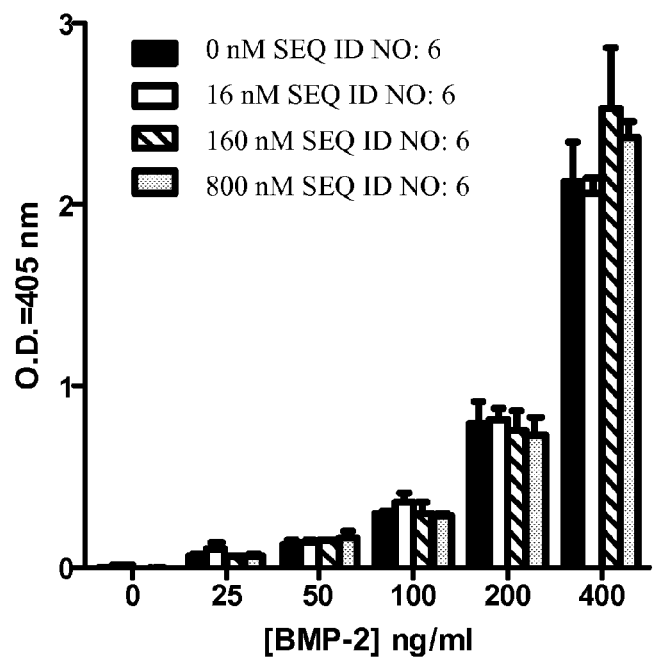
FIG. 7. Functional interference of affinity peptides on BMP-2 receptor binding by assessment of alkaline phosphatase activity of mouse (MCH 1/26) osteoblasts after 3 days in the presence of BMP-2.

FIG. 7 shows that SEQ ID NO: 6 has minimal effect on the ALP production of mouse osteoblasts. This suggests that SEQ ID NO: 6 does not interfere with the bioactivity of BMP-2.

Example 7

Preparation of Foam Collagen Biomatrix

A 40 mg/mL solution of 80% fibrous Type I Collagen (32 mg) and 20% soluble Type I Collagen (8 mg) in water was stirred overnight at 4° C. This suspension was then homogenized in a blender for 3 cycles (30 seconds to 1 min/cycle). Approximately 5 mL were transferred to a mold with the dimensions of 5 cm×5 cm and a height of 0.5 cm. The collagen mixture was leveled with a straight edge spatula to ensure an even height distribution of the collagen. Next, the sample was degassed then lyophilized (Virtis, Gardiner, NY) using a cycle profile shown in Table 3. The samples were then thermally dehydrated using a temperature controlled vacuum chamber. The foam collagen biomatrix was then cut into 6 mm discs using a biopsy punch and stored at room temperature under dry nitrogen purge until ready for use.

TABLE 3

| Temperature (° C.) | Time (minutes) | Pressure (mTorr) |
| --- | --- | --- |
| −40 | 60 | 500 |
| −25 | 300 | 100 |
| −20 | 600 | 50 |
| −10 | 300 | 50 |
| −5 | 180 | 50 |
| 0 | 120 | 50 |
| 10 | 120 | 50 |
| 20 | 120 | 50 |

Example 8

Preparation of Affinity Biomatrix by Conjugation of Affinity Peptide Toward BMP-2 to Foam Collagen Biomatrix For peptide conjugation, a 6 mm collagen foam disc, prepared as described in Example 7, was placed in 1.8 mL of 40% EtOH/50 mM 2-(N-morpholino)ethanesulfonic acid (MES), pH 5.5 in an eppendorf tube and tumbled for 30 min. at room temperature. The disc was removed from the above buffer and placed in 1.8 mL of 40% EtOH/50 mM MES pH 5.5 containing 0.5 mM SEQ ID NO: 23 BMP-2 affinity peptide (conjugation peptide of SEQ ID NO: 6 shown in FIG. 8A). Peptides were prepared using standard, automated Fluorenylmethyloxycarbonyl (Fmoc) solid phase peptide synthesis procedures. The disc was allowed to tumble at room temperature for 1 hour. Next, 10 microliters of a 0.5M EDC stock solution and 10 microliters of a 0.1M Sulfo-NHS stock solution (both in 40% EtOH/50 mMMES pH5.5) was introduced into the eppendorf resulting in final concentrations of 2.5 mM EDC and 0.5 mM Sulfo-NHS (molar equivalents were 1:1:5 for Peptide, Sulfo-NHS and EDC, respectively). The disc was allowed to tumble for 4 hours at room temperature. Next, the disc was rinsed by tumbling in 10 mL of 1×PBS for 30 minutes. This rinse was repeated for a total of three rinse cycles. Lastly, the disc was removed from the PBS and allowed to dry under vacuum on the lyophilizer overnight. Three control samples were also used in the above procedure. 1=Collagen Sponge+Buffer, 2=Collagen Sponge+Peptide/Buffer, and 3=Collagen Sponge+EDC/NHS/Buffer.

Figure 8B:
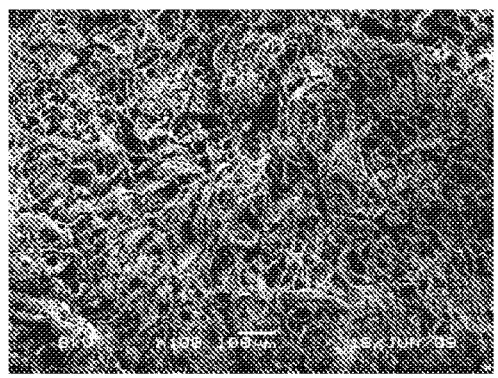
FIG. 8B. Scanning electron microscopy (SEM) image of a collagen affinity biomatrix after coupling of SEQ ID NO: 23.

The microstructure of the peptide-conjugated collagen foam (affinity biomatrix) was analyzed using SEM. A representative image is shown in FIG. 8B. The image shows that the peptide-conjugated collagen foam retains its porous microstructure. For all samples, the supernatants were lyophilized to a dry powder and analyzed using RP-Analytical HPLC. Data indicate that approximately 40% of the BMP-2 affinity peptide (SEQ ID NO: 23) was covalently conjugated to the 6 mm collagen disc.

Example 9

BMP-2 Retention Test

Lyophilized rhBMP-2 was dissolved in 8.4 mL of sterile water resulting in a 1.5 mg/mL suspension of rhBMP-2. For the loading studies, 6 mm diameter affinity biomatrix, as prepared in Example 7 and Example 8, were placed in a 0.2 micrometer filtration eppendorf and loaded with 100 microliters of a 0.4 mg/mL rhBMP-2 solution (250 mM Arginine, 10 mM Histidine, 20 mM $CaCl_2$ (pH 6.5) buffer) and allowed to sit at room temperature for 45 minutes. The affinity biomatrix in the filtration eppendorf was then spun at 3000 rpm for 5 minutes to remove the supernatant. A rhBMP-2 Immunoassay ELISA (R&D Systems (Minneapolis, Minn.) DBP200) was performed using a 1:100000 dilution of the resultant supernatant following the procedure in the product insert. The % rhBMP-2 incorporation was determined by subtracting the amount of rhBMP-2 in the supernatant from the initial loading concentration of BMP-2. As a control, a 6 mm diameter disc of both the affinity peptide-free EDC/NHS crosslinked collagen was used.

Figure 9:
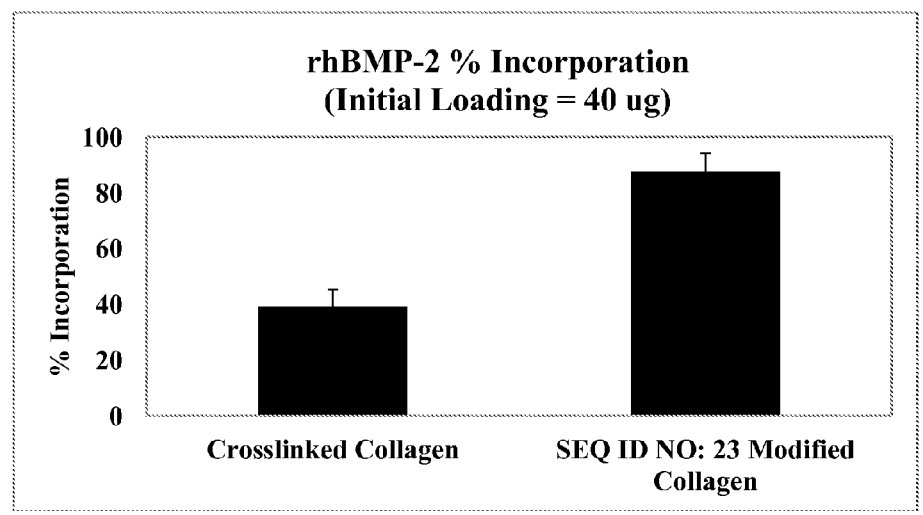
FIG. 9. Percent incorporation of BMP-2 loaded into the collagen biomatrix and collagen affinity biomatrix discs.

Data in FIG. 9 shows the affinity biomatrix loads approximately 90% by weight of the total BMP-2 (40 micrograms) as compared to the crosslinked collagen discs which load approximately 40% by weight.

Example 10

In Vitro BMP-2 Release from Collagen Discs

In this experiment, we have evaluated the in vitro controlled release of BMP-2 from the affinity biomatrix under simulated physiological conditions. For the release studies, 6 mm diameter discs of affinity biomatrix as prepared by the methods described in Example 7 and Example 8, were placed in a well of a 24 well cell culture plate. The sponges were loaded with 40 microliters of a 1.5 mg/mL rhBMP-2 solution and allowed to sit at room temperature for 15 minutes. A 6 mm diameter disc of the affinity peptide-free EDC/NHS crosslinked collagen prepared in Example 8 was used as a control. The loaded collagen sponges were then transferred to a well of a 24 well cell culture plate containing 1.5 mL of PBS supplemented with human serum albumin (HSA) at a concentration of 1 mg/mL. At the respective time points, the media was removed and transferred to an eppendorf tube then frozen at −20° C. The wells containing the collagen discs were replenished with 1.5 mL of fresh 0.1% HSA in PBS. A rhBMP-2 Immunoassay ELISA (R&D Systems (Minneapolis, Minn.) DBP200) was performed at each time point using a 1:1000 dilution of the release media following the procedure in the product insert. The amount of rhBMP-2 release from the respective disc was determined by using a standard curve.

Figure 10:
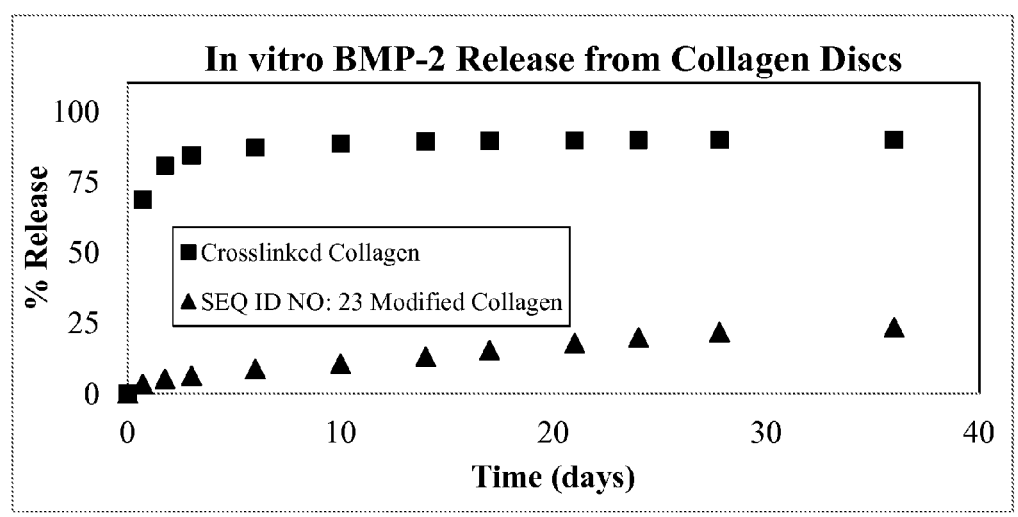
FIG. 10. In vitro release study showing the amount of BMP-2 released from the collagen biomatrix and collagen affinity biomatrix discs over a time period of 36 days.

Data in FIG. 10 shows the affinity biomatrix controlled release device has a cumulative release of rhBMP-2 of approximately 25% by weight at the 36 day time point whereas the EDC/NHS crosslinked collagen sponge releases approximately 90% by weight. The initial burst release of rhBMP-2 from the affinity biomatrix controlled release device is significantly reduced as compared to the EDC/NHS crosslinked collagen sponge.

Example 11

Mutant Phage ELISA

Site-directed mutagenesis was performed on affinity peptide SEQ ID NO: 3 and SEQ ID NO: 6 respectively, to obtain an understanding of the amino acids which are important for binding to BMP-2. Mutants of SEQ ID NO: 3 and SEQ ID NO: 6 were constructed by performing a serine scan where residues of the wild type were substituted with serine. FIG. 12 shows the mutant sequences that were tested to identify more specific amino acid sequences that are responsible for the specific affinity toward BMP-2. SEQ ID NO: 24 through SEQ ID NO: 28 are mutants of SEQ ID NO: 3. SEQ ID NO: 29 through SEQ ID NO: 32 are mutants of SEQ ID NO: 6.

The respective custom oligonucleotide was obtained from Integrated DNA Technologies. The oligonucletides were inserted into the pIX gene using standard protocols. First, the oligonucletides were phosphorylated using T4 polynucleotide kinase. Next, the phosphorylated oligonucletides were annealed to the ssDNA template. Using the Kunkel method, the annealed DNA was ligated using T4 DNA ligase and T7 DNA polymerase. The resultant DNA was isolated using isopropanol precipitation and a gel was run to confirm the reaction. Lastly, electro-competent *E. coli* cells were transformed with the purified DNA and were plated out onto 2xYT/Tet/Xgal agar plates and allowed to grow overnight to isolate single colonies. An aliquot of the transformed cells was allowed to grow overnight at 37° C. while shaking in 50 mL 2xYT/tet media. The phage were then PEG precipitated following the procedure in Example 1. A phage titration was performed to determine the concentration of phage for the ELISA assay as described in Example 2. ELISA assays were performed following the procedure in Example 3.

Figure 11A:
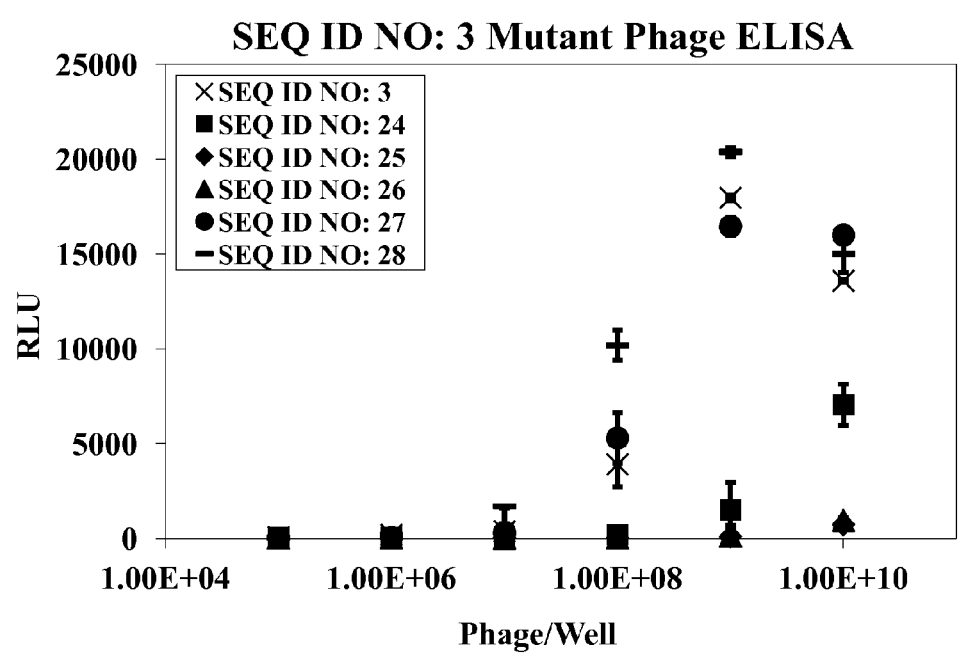
FIG. 11A. Mutant phage ELISA showing fragments of SEQ ID NO: 3 that bind to BMP-2.
Figure 11B:
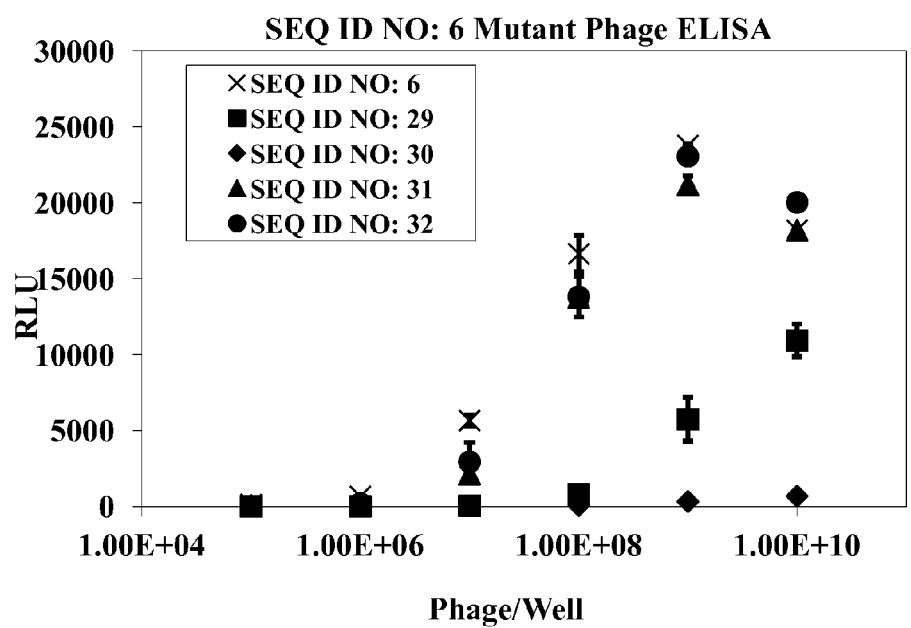
FIG. 11B. Mutant phage ELISA showing fragments of SEQ ID NO: 6 that bind to BMP-2.

Mutant phage ELISA assay data (FIG. 11A and FIG. 11B) show evidence that fragments of SEQ ID NO: 3 and fragments of SEQ ID NO: 6 bind to BMP-2. More specifically, SEQ ID NO: 33, a fragment of SEQ ID NO: 3, and SEQ ID NO: 34, a fragment of SEQ ID NO: 6 are important for binding to BMP-2 and are shown in FIG. 12.

Example 12

In Vitro BMP-2 Release from Collagen Discs

In this experiment, we have evaluated the in vitro controlled release of BMP-2 from the affinity biomatrix under simulated physiological conditions as described in Example 10, however we used PBS supplemented with heat inactivated fetal bovine serum (FBS) instead of PBS alone. For the release studies, 6 mm diameter discs of affinity biomatrix as prepared by the methods described in Example 7 and Example 8, were placed in a well of a 24 well cell culture plate. The sponges were loaded with 40 microliters of a 1.5 mg/mL rhBMP-2 solution and allowed to sit at room temperature for 15 minutes. A commercially available collagen disc was used as a control. The loaded collagen sponges were then transferred to a well of a 24 well cell culture plate containing 1.5 mL of PBS supplemented with heat inactivated fetal bovine serum (FBS). At the respective time points, the media was removed and transferred to an eppendorf tube then frozen at −20° C. The wells containing the collagen discs were replenished with 1.5 mL of fresh 2% FBS in PBS. An rhBMP-2 Immunoassay ELISA (R&D Systems (Minneapolis, Minn.) DBP200) was performed at each time point using a 1:1000 dilution of the release media following the procedure in the product insert. The amount of rhBMP-2 release from the respective disc was determined by using a standard curve.

Figure 13:
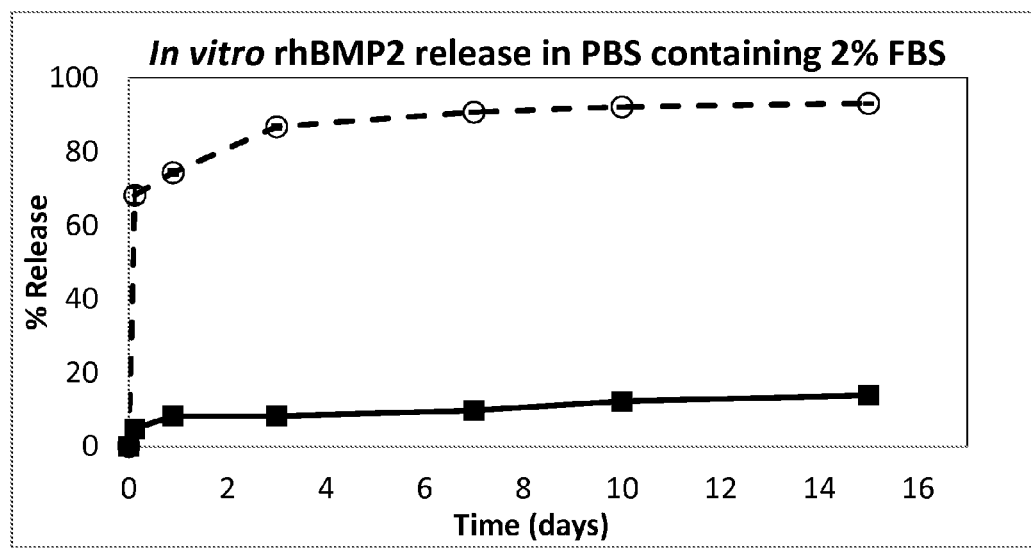
FIG. 13. In vitro release study, performed in phosphate buffered saline (PBS) containing 2% heat inactivated fetal bovine serum (FBS), showing the amount of BMP-2 released from the collagen biomatrix and collagen affinity biomatrix discs over a time period of 15 days.
Figure 14:
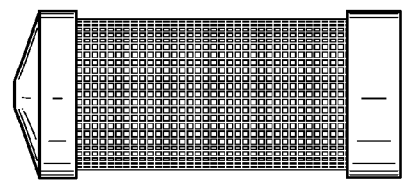
FIG. 14. Image of the stainless steel chamber used for the in vivo cage implant testing system.
Figure 15:
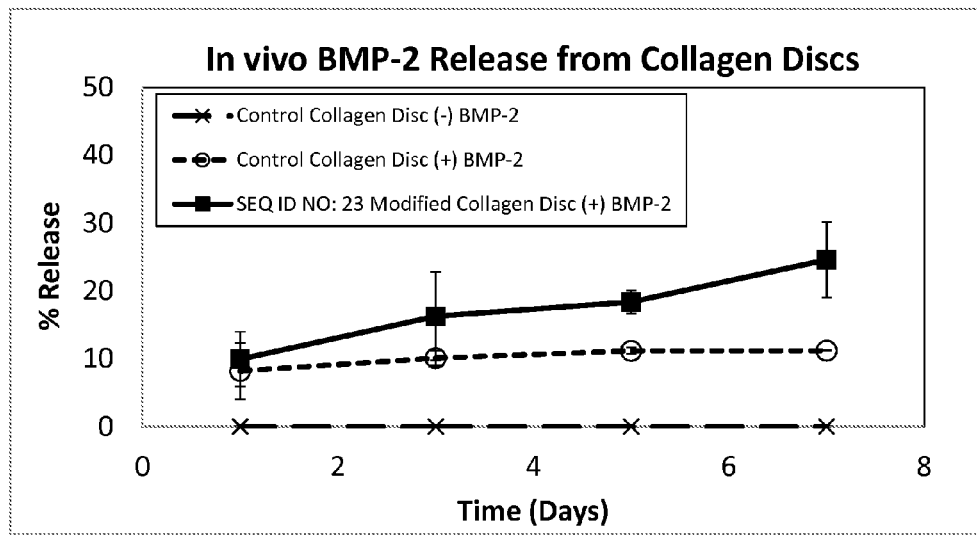
FIG. 15. In vivo release study showing the amount of BMP-2 released from the collagen biomatrix and collagen affinity biomatrix discs over a time period of 7 days.

Data in FIG. 13 shows the affinity biomatrix controlled release device has a cumulative release of rhBMP-2 of approximately 15% by weight at the 15 day time point whereas the commercially available collagen sponge releases approximately 95% by weight. The initial burst release of rhBMP-2 from the affinity biomatrix controlled release device is significantly reduced as compared to the commercially available collagen sponge.

Example 13

In Vivo BMP-2 Release from Collagen Discs

A cage implant testing system was used to evaluate the in vivo release of BMP-2 from the affinity biomatrix. An example of using the cage implant system to study the controlled release of bioactive agents in an in vivo environment is described in Paula S. Leppert and Joseph A. Fix, *Subcutaneous Tissue Cages for Examination of Slow Release of Materials from Long Term Implants*, Biomaterials, Volume 11, 1990, page 46-49. These methods were adapted to measure the in vivo release of BMP-2 from the affinity biomatrix.

This in vivo study complied with all applicable regulations governing the care and use of laboratory animals. Animal welfare for this study was in compliance with the United States Department of Agriculture's (USDA) Animal Welfare Act (9 CFR Parts 1, 2 and 3). The Guide for the Care and Use of Laboratory Animals (Institute of Laboratory Animal Resources, National Academy Press, Washington, D.C., 1996) was followed. Seven to eight week old, male rats, specifically an outbred multipurpose breed of albino rats sold under the trade name SPRAGUE DAWLEY (Harlan Laboratories, Inc., Indianapolis, Ind.) species Crl:CD were used for this in vivo study. Animals were housed individually in polyboxes with direct contact bedding. Fluorescent lighting was provided for approximately 12 hours per day. Temperature and humidity were monitored and recorded daily and were maintained to the maximum extent possible between 64° C. to 79° C. and 30% to 70%, respectively. The rats' basal diet consisted of a certified rodent diet supplied ad libitum. Tap water was supplied ad libitum via an automatic water system. A brief description of the study design can be found in Table 4.

TABLE 4

| Group | Number of Rats | Biomatrix | Dose and Description |
|---|---|---|---|
| 1 | 5 | Collagen Disc | +PBS |
| 2 | 5 | Collagen Disc | +BMP-2 |
| 3 | 5 | SEQ ID NO: 23 Modified Collagen Disc | +BMP-2 |

Cage implants (length=25 millimeters, diameter=10 millimeters) were manually constructed using 316 gauge, 46 mesh (0.0055 inch wire diameter) stainless steel (Newark Wire Cloth Company, Clifton, N.J.). Cage implants were depyrogenized using 0.1 M sodium hydroxide and washed thoroughly with water. One end of the cage implant was closed by casting a silicone elastomer (MED6215, NuSil Technology, LLC, Toms River, NJ) cap around the chamber end using a predrilled polytetrafluoroethylene (PTFE) block. A custom molded silicone elastomer stopper (Wacker LR3003/40, Albright Technologies Inc., Leominster, MA) cap was used to close the open end of the cage after the addition of the respective biomatrix. Prior to loading the cages with the discs the caps and cages were autoclaved.

Collagen discs were prepared under aseptic conditions following the procedure in Example 7. Next, the 6 mm diameter discs of collagen were sterilized using E-beam radiation (25 kGy). The affinity biomatrix was prepared under aseptic conditions using the methods described in Example 8. The samples were then lyophilized in a sterile chamber using the lyophilization method shown in Table 3. A 6 mm diameter disc of the affinity peptide-free commercially available collagen was used as a control.

Prior to implantation, the dry, biomatrix was placed into the chamber and sutured in place with a non-absorbable suture. The discs were then loaded with 100 microliters of a sterile solution of BMP-2 at a dose of 30 micrograms per disc. Anesthesia was induced in each rat using inhalation anesthesia (isoflurane). Ophthalmic ointment was applied to the eyes to prevent drying of the tissue during the anesthetic period. Each animal was administered buprenorphine hydrochloride (0.05 mg/kg, SC) for pain and Lactated Ringers Solution (LRS, 1-5 mL) for fluid homeostasis. After induction of anesthesia, the surgical site of the animal from the dorsal cervical area to the dorsal lumbar area was clipped free of hair by using an electric animal clipper equipped with a vacuum system. The area around the site of surgery was scrubbed with chlorhexidine diacetate, rinsed with alcohol, dried, and painted with an aqueous iodophor solution of 1-% available iodine. The anesthetized animal was delivered to the operating table where a sterile surgical drape was applied to the prepared area using aseptic technique. During surgery the animal was maintained with isoflurane by mask while under an evacuation system.

The sterile, cage implant containing the BMP-2 loaded disc was implanted into the subcutaneous space of each rat. A skin incision was made on the left dorsal thorax. A subcutaneous pocket was created via blunt dissection, just large enough to accommodate the wound chamber, on the dorsum of the rats. The cage implant was placed in the subcutaneous pocket, minimizing void subcutaneous space. The cage implant was inserted with the end containing the sample, nearest the silicone end-cap and farthest the silicone stopper, closest to the incision site. The proximal end of the cage was inserted a minimum of 1 cm distance from the incision line to avoid irritation. The cage implant was sutured with non-absorbable suture to the underlying muscle, and the incision was closed using non-absorbable suture.

Wound exudate was collected on days 1, 3, 5 and 7 post-implantation. Prior to fluid collection, animals were mildly anesthetized using carbon dioxide/oxygen and isoflurane. Briefly, a 21 G needle was inserted into the middle of the silicone stopper furthest away from the incision site. The rat was held in an upright position to allow for the fluid to drain into the syringe. The syringe was aspirated slowly until a collection volume of 300 microliters was achieved. Samples were frozen at −80 degrees Celsius until analysis using an rhBMP-2 Immunoassay ELISA. On completion of the study, animals were euthanized by placing them in a pre-charged carbon dioxide chamber and subjecting them to inhalation of 100% carbon dioxide. Euthanasia was confirmed by observation for visual signs of respiration and palpation of the heart.

Data in FIG. 13 shows the affinity biomatrix controlled release device consistently releases BMP-2 over a seven day time period. On day 5 and day 7, the affinity biomatrix has a statistically significant difference of BMP-2 released from the disc as compared to the control collagen disc.

We claim:

1. An isolated affinity peptide toward bone morphogenic protein-2 (BMP-2) selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10.

2. An affinity biomatrix comprising a biocompatible, biodegradable polymer and at least one isolated affinity peptide toward bone morphogenic protein-2 (BMP-2) selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10, wherein the at least one affinity peptide toward BMP-2 is covalently attached to the biocompatible, biodegradable polymer.

3. The affinity biomatrix of claim 2, wherein the biocompatible, biodegradable polymer is a natural polymer, wherein the natural polymer is selected from the group consisting of collagen, elastin, keratin, silk, polysaccharides, glucosaminoglycans (GAGs), and combinations thereof.

4. The affinity biomatrix of claim 3, wherein the natural polymer is collagen.

5. A controlled release device comprising:
  a) an affinity biomatrix comprising a biocompatible, biodegradable polymer and at least one isolated affinity peptide toward bone morphogenic protein-2 (BMP-2) selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10, wherein the at least one affinity peptide toward BMP-2 is covalently attached to the biocompatible, biodegradable polymer; and b) BMP-2.

6. The controlled release device of claim 5, wherein the device is in a form selected from the group consisting of sponges, particles, injectable gels, injectable liquids, membranes, films, fibers and fiber based scaffolds.

7. A kit comprising:

a) an affinity biomatrix comprising a biocompatible, biodegradable polymer and at least one isolated affinity peptide toward bone morphogenic protein-2 (BMP-2) selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10, wherein the at least one affinity peptide toward BMP-2 is covalently attached to the biocompatible, biodegradable polymer; and b) BMP-2.

* * * * *

```
                        SEQUENCE LISTING

<160> NUMBER OF SEQ ID NOS: 34

<210> SEQ ID NO 1
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ala Gly Leu Pro Leu Gln Ser Met Ser Arg Leu Ser Tyr Asp Ser Leu
1               5                   10                  15

Ser

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ala Gly Pro Pro Gly Pro Tyr Ile Ala Ala Ser Ala Phe Leu Ala Leu
1               5                   10                  15

Lys

<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Gly Tyr Thr Ser Phe Ala Leu Leu Lys Ser Ala Glu Ser Thr Leu
1               5                   10                  15

Pro

<210> SEQ ID NO 4
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ala Gly Phe Arg Trp Trp His Thr Gln Pro Ala His Thr Leu Ser Tyr
1               5                   10                  15

Thr

<210> SEQ ID NO 5
<211> LENGTH: 17
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 5

Ala Gly Tyr Arg Arg Pro Ile Gln Pro Gly Pro Glu Ala Val Ser Leu
1               5                   10                  15

Leu

<210> SEQ ID NO 6
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ala Gly Arg Asp Ser Phe Asn Leu Leu Thr Ser Ser Pro Leu Pro Ser
1               5                   10                  15

Thr

<210> SEQ ID NO 7
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ala Gly Tyr Arg Cys Ser Glu Leu Pro Leu Tyr Cys Ser Thr
1               5                   10

<210> SEQ ID NO 8
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ala Gly Ser Trp Cys Thr His Pro Ala Ile Gly Cys Leu Ser
1               5                   10

<210> SEQ ID NO 9
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ala Gly Ser Pro Cys Ser Pro Gly Gln Leu Pro Leu Cys Pro Ala
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10
```

```
Ala Gly Leu Gln Cys Ser Pro Pro Leu Pro Leu Tyr Cys Glu Pro
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ala Gly Pro Arg Cys Pro Pro Met His Phe Ser Val Cys Leu Ser
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ala Gly Ala Ser Cys Ser Pro Gly Leu His Pro Leu Cys Pro Gly
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ala Gly Ser Thr Cys Ile Pro Ser Met Thr Pro Leu Cys Pro Ser
1               5                   10                  15

<210> SEQ ID NO 14
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ala Gly Arg Glu Cys Leu Pro Gln Phe Gly Leu Pro Leu Cys Pro Asp
1               5                   10                  15

<210> SEQ ID NO 15
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ala Gly Ser Val Cys Leu Ala Gln Tyr Ser Ala Thr Pro Leu Cys Pro
1               5                   10                  15

His

<210> SEQ ID NO 16
<211> LENGTH: 17
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 16

Ala Gly Pro Asp Cys Arg Leu Ser Pro Leu Gln Pro Ala Val Cys Val
1               5                   10                  15
Trp

<210> SEQ ID NO 17
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ala Gly Ala His Cys Leu Arg Asp His Met Gly Leu Thr Ser Cys Ile
1               5                   10                  15
Pro

<210> SEQ ID NO 18
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ala Gly Arg Leu Cys His Ala Thr Val Asp Gly Val Ala Val Gly Cys
1               5                   10                  15
Leu Thr

<210> SEQ ID NO 19
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ala Gly Thr Val Cys Pro Pro Asp Leu Thr Gly Leu Thr Ala Ala Cys
1               5                   10                  15
Tyr Tyr

<210> SEQ ID NO 20
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ala Gly Thr Leu Cys Gly Val Asp Asp Tyr Thr Gly Leu Thr Gly Cys
1               5                   10                  15
Leu Ala

<210> SEQ ID NO 21
<211> LENGTH: 18
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 21

Ala Gly Ile Arg Cys Pro Val Asp Ala Ile Gly Leu Thr Ala Asn Cys
1               5                   10                  15

Ser Tyr

<210> SEQ ID NO 22
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ala Gly Arg Ser Cys Tyr Arg Glu Pro Ser Thr Met Leu Tyr Ala Cys
1               5                   10                  15

Thr Ala

<210> SEQ ID NO 23
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac-
<220> FEATURE:
<223> OTHER INFORMATION: C-term -OH

<400> SEQUENCE: 23

Ala Gly Arg Asp Ser Phe Asn Leu Leu Thr Ser Ser Pro Leu Pro Ser
1               5                   10                  15

Thr Ser Gly Gly Ser Gly Gly Ser Gly Gly
            20                  25

<210> SEQ ID NO 24
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ala Gly Ser Ser Ser Phe Ala Leu Leu Lys Ser Ala Glu Ser Thr Leu
1               5                   10                  15

Pro

<210> SEQ ID NO 25
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ala Gly Ser Ser Ser Phe Ala Leu Leu Lys Ser Ala Glu Ser Thr Leu
1               5                   10                  15

Pro
```

```
<210> SEQ ID NO 26
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ala Gly Tyr Thr Ser Phe Ala Leu Ser Ser Ser Ala Glu Ser Thr Leu
1               5                   10                  15

Pro

<210> SEQ ID NO 27
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ala Gly Tyr Thr Ser Phe Ala Leu Leu Lys Ser Ala Glu Ser Ser Ser
1               5                   10                  15

Ser

<210> SEQ ID NO 28
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ala Gly Tyr Thr Ser Phe Ala Leu Leu Lys Ser Ala Glu Ser Ser Ser
1               5                   10                  15

Ser

<210> SEQ ID NO 29
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ala Gly Ser Ser Ser Phe Asn Leu Leu Thr Ser Ser Pro Leu Pro Ser
1               5                   10                  15

Thr

<210> SEQ ID NO 30
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ala Gly Arg Asp Ser Phe Asn Leu Ser Ser Ser Pro Leu Pro Ser
1               5                   10                  15

Thr
```

```
<210> SEQ ID NO 31
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ala Gly Arg Asp Ser Phe Asn Leu Leu Thr Ser Ser Ser Ser Pro Ser
1               5                   10                  15

Thr

<210> SEQ ID NO 32
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Ala Gly Arg Asp Ser Phe Asn Leu Leu Thr Ser Ser Pro Leu Ser Ser
1               5                   10                  15

Ser

<210> SEQ ID NO 33
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ala Gly Tyr Thr Ser Phe Ala Leu Leu Lys Ser
1               5                   10

<210> SEQ ID NO 34
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ala Gly Arg Asp Ser Phe Asn Leu Leu Thr Ser
1               5                   10
```